US007151091B2

(12) United States Patent
Scheele et al.

(10) Patent No.: US 7,151,091 B2
(45) Date of Patent: *Dec. 19, 2006

(54) COMPOSITIONS AND METHODS FOR PREVENTING INFECTION

(75) Inventors: George A. Scheele, La Jolla, CA (US); James E. Hildreth, Woodstock, MD (US)

(73) Assignees: The Johns Hopkins University, Baltimore, MD (US); La Jolla Biosciences LLC, La Jolla, CA (US)

( * ) Notice: Subject to any disclaimer, the term of this patent is extended or adjusted under 35 U.S.C. 154(b) by 245 days.

This patent is subject to a terminal disclaimer.

(21) Appl. No.: 10/667,727

(22) Filed: Sep. 22, 2003

(65) Prior Publication Data

US 2004/0209844 A1    Oct. 21, 2004

Related U.S. Application Data

(60) Provisional application No. 60/412,399, filed on Sep. 20, 2002.

(51) Int. Cl.
*A01N 43/04*    (2006.01)
*A61K 31/70*    (2006.01)
*C08B 37/16*    (2006.01)

(52) U.S. Cl. .................... 514/58; 514/54; 514/841; 514/931; 514/934; 536/102; 536/123.1

(58) Field of Classification Search .................. 514/54, 514/58, 841, 931, 934; 536/102, 103, 123.1
See application file for complete search history.

(56) References Cited

U.S. PATENT DOCUMENTS 6,068,851 A * 5/2000 Bergeron et al. ........... 424/424
6,239,182 B1 * 5/2001 Zaneveld et al. ........... 514/764
6,835,717 B1 * 12/2004 Hildreth ..................... 514/58

OTHER PUBLICATIONS

Khanna et al. The Journal of Clinical Investigation (Jan. 2002), vol. 109, No. 2, pp. 205-211.*
Nguyen et al. Blood (Jun. 2002), vol. 99, No. 12, pp. 4298-4306.*
Leyder et al. J. Med. Chem. (1998), vol. 41, pp. 4927-4932.*
Khanna et al. The Journal of Clinical Investigation (2002), vol. 109, pp. 205-211.*
Biggar et al. Lancet (1996), vol. 347, p. 1647.*
Kuhn et al. Pediatr Drugs (2002), vol. 3, pp. 191-203.*
Leydt et al. J. Med. Chem. (1998), vol. 41, pp. 4927-4932.*

* cited by examiner

*Primary Examiner*—Patrick Lewis
(74) *Attorney, Agent, or Firm*—DLA Piper US LLP

(57) ABSTRACT

This invention relates to cholesterol-sequestering agents and methods of using cholesterol-sequestering agents to prevent infection. The compositions of the invention can be used to reduce or prevent maternal to fetal transmission of a microorganism and/or to reduce or eliminate a microorganism present in a blood sample or a blood product.

29 Claims, No Drawings

COMPOSITIONS AND METHODS FOR PREVENTING INFECTION

CROSS REFERENCE TO RELATED APPLICATIONS

This application claims priority from U.S. Provisional Application No. 60/412,399, filed Sep. 20, 2002. The prior application is incorporated herein by reference in its entirety.

STATEMENT AS TO FEDERALLY SPONSORED RESEARCH

This invention was made with Government support under grant numbers HD-40772, AI-31806, and HD-39613 awarded by the National Institutes of Health. The Government may have certain rights in the invention.

TECHNICAL FIELD

This invention relates to methods and compositions for preventing infection, and more particularly to methods and compositions using cholesterol-sequestering agents.

BACKGROUND

Approximately 7,000 human immunodeficiency virus (HIV)-infected women give birth in the United States each year. Without treatment, about one-fourth of them transmit the virus to their children. The anti-HIV drug zidovudine (AZT), given to HIV-infected pregnant women before and during childbirth and to their infants after childbirth, reduces HIV transmission by as much as two-thirds. Treatment with AZT is now the standard of care in the U.S. for preventing HIV infection in infants. However, additional means are needed for the prevention of maternal to fetal transmission of HIV and other envelope viruses both in the U.S. and worldwide.

SUMMARY

In one aspect, the invention features a method of reducing or preventing maternal to fetal transmission of a microorganism. The method includes the steps of: selecting a pregnant individual diagnosed as being infected with a microorganism; and administering to the birth canal of the individual a composition containing a cholesterol-sequestering agent, wherein the composition is administered prior to a vaginal birth of a fetus, and wherein an amount of the cholesterol-sequestering agent effective to reduce or prevent maternal to fetal transmission of the microorganism remains present in the birth canal during the vaginal birth.

In another embodiment, the invention features a method of reducing or preventing maternal to fetal transmission of a microorganism. The method includes the steps of: selecting a pregnant individual diagnosed as being infected with a microorganism; and administering to the individual a composition containing a cholesterol-sequestering agent, wherein the composition is administered to the individual at a site of a surgical incision for a cesarean section birth of a fetus, and wherein an amount of the cholesterol-sequestering agent that is effective to reduce or prevent maternal to fetal transmission of the microorganism remains present at the site during the cesarean section birth.

A "cholesterol-sequestering agent" refers to a compound that binds to cholesterol and extracts and depletes cholesterol from a biological membrane such as a plasma membrane or a membrane of an envelope virus. A cholesterol-sequestering agent preferentially extracts cholesterol from lipid rafts present in a biological membrane. The cholesterol-sequestering agent can be, for example, a cyclodextrin. In one example, the cholesterol-sequestering agent is a beta-cyclodextrin such as 2-OH-propyl-beta-cyclodextrin.

"Birth canal" refers to the passageway through which the fetus is expelled during parturition, leading from the uterus through the cervix, vagina, and vulva.

The microorganism can be, for example, a bacterium (e.g., anthrax or chlamydia), a mycobacterium (e.g., mycobacterium tuberculosis), a virus (e.g., an envelope virus or a non-envelope virus, e.g., a protein coated virus such as picorna virus or a papilloma virus), a fungus, or a protozoan. In some embodiments, the microorganism enters a cell of a host by endocytosis during at least a portion of its life cycle.

In one example, the microorganism is an envelope virus. The envelope virus can be, for example, a human immunodeficiency virus (HIV) such as HIV-1 or HIV-2; a human herpes virus (HHV) such as HHV1, HHV2, HHV3, HHV4, HHV5, HHV6, HHV7, or HHV8; a hepatitis virus such as hepatitis B virus, hepatitis C virus, or hepatitis D virus; a pox virus such as a small pox virus or molluscum contagiosum virus; an orthomyxovirus such as an influenza virus types A, B, or C; a paramyxovirus such as a mumps virus or a parainfluenza virus type 1, 2, 3, or 4; a human T-cell lymphotropic virus (HTLV) such as HTLV type I or II; a togaviruses such as rubella virus, yellow fever virus, or sinbis virus; ebola virus; or a coronavirus such as severe acute respiratory syndrome (SARS) virus. The envelope virus can be any type or any strain of a given envelope virus. Non-limiting examples of envelope viruses and various types are described herein.

In one embodiment, the envelope virus is a human immunodeficiency virus (HIV). In other embodiments, the envelope virus is a human herpes virus (e.g., HHV1 or HHV2 for the treatment of *Herpes labialis* and *Herpes genitalis*), a hepatitis virus, a pox virus, an influenza virus, a parainfluenza virus, or a human T-cell lymphotropic virus (HTLV).

In some embodiments, the composition used in the methods is formulated as a cream, gel, or lubricant.

For vaginal birth applications, the composition is administered to the birth canal of the pregnant individual before birth. For example, the composition can be administered to the birth canal at least 1, 2, 3, 4, 5, 6, 12, 24, 48, 72, or more hours before birth. In some examples, the composition is administered to the birth canal less than 72, 48, 24, 12, 6, 5, 4, 3, 2, or 1 hour before birth. In some embodiments, a plurality of administrations of the composition are applied to the birth canal within a period of one week prior to the birth. For example, a plurality of administrations of the composition can applied to the birth canal within a period of 24, 12, or 6 hours prior to the birth.

Some embodiments of the methods described herein contain an additional step of administering to the individual an amount of an antimicrobial agent, e.g., antiviral agent, effective to reduce load of microorganism, e.g., virus, in the peripheral blood of the individual. Examples of antiviral agents (e.g., anti-HIV agents) include a nucleoside reverse transcriptase inhibitor, a non-nucleoside reverse transcriptase inhibitor, a protease inhibitor, a fusion inhibitor, and an integrase inhibitor.

Some embodiments of the methods described herein contain an additional step of intravenously administering to the individual prior to the birth an amount of a cholesterol-sequestering agent effective to reduce viral load in the individual.

In some embodiments, after cutting of the umbilical cord a newborn is contacted with an amount of the cholesterol-sequestering agent effective to reduce or prevent transmission of the microorganism to the newborn. In addition, the cholesterol-sequestering agent can be administered to the newborn orally and/or intravenously. In some instances the cholesterol-sequestering agent is administered to the fetus intravenously before birth.

In another aspect, the invention features a method of treating blood or a blood product. The method includes the steps of: providing a sample containing blood or a blood product; and contacting the sample in vitro with a composition containing an amount of a cholesterol-sequestering agent effective to reduce the load of a microorganism, if present, in the sample, wherein the sample is maintained after the contacting step in a sterile vessel.

The term "blood product" refers to a therapeutic material made from blood and includes both blood components and plasma fractions.

The cholesterol-sequestering agent can be any of the compounds described herein, e.g., a beta-cyclodextrin such as 2-OH-propyl-beta-cyclodextrin.

The microorganism can be any of the microorganisms described herein. For example, the microorganism can be an envelope virus such as a human immunodeficiency virus (HIV). In other embodiments, the microorganism is an envelope virus such as a human herpes virus, a hepatitis virus, a pox virus, an influenza virus, a parainfluenza virus, a human T-cell lymphotropic virus (HTLV), a West Nile virus, or a SARS virus.

The sample can contain, for example, whole blood, e.g., human whole blood; plasma; serum; enriched red blood cells; enriched platelets; or protein (e.g., an immunoglobulin or clotting factor) purified from whole blood.

In some embodiments, the method includes an additional step of introducing the sample into an individual following the contacting of the sample with the composition.

In some embodiments, the method includes an additional step of removing or depleting white blood cells from the sample prior to introducing the sample into the individual.

The sample can optionally be identified as containing an envelope virus.

In some embodiments, the method includes an additional step of testing the sample for the presence of the envelope virus following the contacting with the composition.

In another aspect, the invention features a composition containing a cholesterol-sequestering agent and an amount of blood or a blood product suitable for administration to an individual having a blood-related disorder or deficiency, wherein the composition is maintained in a sterile vessel.

The composition can contain, for example, whole blood, e.g., human whole blood; plasma; serum; enriched red blood cells; enriched platelets; or protein (e.g., an immunoglobulin or clotting factor) purified from whole blood.

The composition (e.g., a composition containing whole blood) can additionally contain an agent, such as an anticoagulant, that promotes the storage of the blood or blood product. In some embodiments, the composition is frozen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

The present invention provides methods and compositions for preventing an infection by microorganisms such as envelope viruses. The methods and compositions of the invention make use of a cholesterol-sequestering agent that can have one or more of several possible effects on a microorganism. For some microorganisms such as envelope viruses, a cholesterol-sequestering agent may cause the lysis of the virus. By removing cholesterol from a viral membrane, a cholesterol-sequestering agent not only disrupts the ordered structure of membrane elements, but further destroys the integrity of the membrane itself leading to disruption of the viral membrane and leakage of viral contents, an irreversible process that inactivates the viral particle. Accordingly, a cholesterol-sequestering agent can cause a direct reduction in viral load in a biological sample. In other instances, a cholesterol-sequestering agent can block the fusion of a virus with the plasma membrane and/or block the budding of the virus from lipid rafts on the membrane of the infected cell. In some instances, a cholesterol-sequestering agent may block the uptake of an intracellular pathogen by blocking endocytosis in a cell. Accordingly, a cholesterol-sequestering agent can be used to reduce or prevent maternal to fetal transmission of a microorganism and/or to reduce or eliminate a microorganism present in a blood sample or a blood product.

Cholesterol-Sequestering Agent

Any cholesterol-sequestering agent can be used in the methods and compositions described herein. A cholesterol-sequestering agent binds to cholesterol and extracts and depletes cholesterol from a biological membrane, such as a plasma membrane or a membrane of an envelope virus. A cholesterol-sequestering agent preferentially extracts cholesterol from lipid rafts present in a biological membrane.

Examples of cholesterol-sequestering agents include compounds such as cyclodextrins, nystatin, and filipin. Cyclodextrins include both naturally occurring cyclodextrins, e.g., alpha, beta, and gamma cyclodextrins, as well as derivatives of naturally occurring cyclodextrins. Non-limiting examples of derivatives of naturally occurring cyclodextrins include derivatives of beta cyclodextrin such as hydroxypropyl beta cyclodextrin, carboxy-methyl beta cyclodextrin, and methyl beta cyclodextrin. For a detailed description on cyclodextrins and derivatives thereof, see, e.g., Parrish, M. A. "Cyclodextrins—a Review." Sterling Organics Ltd., Newcastle-Upon-Tyne, England; and cyclodex.com.

Beta cyclodextrin, a simple sugar ring structure containing seven alpha (1–4) glucopyranose units, has the ability to rapidly extract cholesterol from lipid rafts, thereby disrupting their ordered membrane structure. As a result of cholesterol removal, lipid rafts are dispersed in the plane of the membrane and the mechanisms responsible for entry and exit of envelop viruses from target cells are abolished.

Beta cyclodextrin has a particularly high affinity for cholesterol. When used at concentrations ranging from 5–100 mM, 2-OH-propyl-beta-cyclodextrin removes membrane cholesterol within minutes. At the molecular level, beta cyclodextrin resembles a toroid or cup-like structure with openings at both the top and bottom. The toroid structure contains hydrophilic groups on the exterior surface and hydrophobic groups on the interior surface. The hydrophylic groups confer solubility in aqueous medium while the hydrophobic groups form the hydrophobic pocket that binds the cholesterol.

Hydroxypropyl beta cyclodextrin is an example of a derivative of beta cyclodextrin that can be used in the methods of the invention. Hydroxypropyl beta cyclodextrin is a partially substituted poly(hydroxpropyl) ether of beta cyclodextrin. The basic closed circular structure of beta cyclodextrin is maintained in hydroxypropyl beta cyclodextrin. The glycosidic oxygen forming the bond between the adjacent glucose monomers and the hydrogen atoms lining the cavity of the cyclodextrin impart an electron density and hydrophobic character to the cavity. Organic compounds interact with the walls of the cavity to form inclusion complexes. The hydroxyl groups and the hydroxypropyl groups are on the exterior of the molecule and interact with water to provide the increased aqueous solubility of the hydroxypropyl beta cyclodextrin and the complexes made with the hydroxypropyl beta cyclodextrin. For a detailed description of the structure of hydroxypropyl beta cyclodextrin, see, e.g., Muller et al. (1986) "Hydroxypropyl-B-cyclodextrin derivatives: Influence of average degree of substitution on complexing ability and surface activity" J. Pharm. Sci. 75.

Treatment of Blood and Blood Products

A cholesterol-sequestering agent can be used to treat blood or a blood product to inactivate a microorganism such as an envelope virus contained therein. In general, a sample containing blood or a blood product is contacted in vitro with a composition containing an amount of a cholesterol-sequestering agent effective to reduce the load of a microorganism, if present, in the sample. In these methods, the sample is generally maintained in a sterile environment that permits the later introduction of the blood or blood product into an individual.

A sample containing blood or a blood product can be treated according to the methods described herein to inactivate a microorganism such as an envelope virus, if present, in the sample. The methods can optionally include an additional step of testing the sample for the presence of the microorganism before and/or after the treatment with the cholesterol-sequestering agent.

In embodiments where testing for the microorganism is performed prior to contacting the sample with a cholesterol-sequestering agent, the result of the testing can be used as an indication as to whether the sample should subsequently be treated with the cholesterol-sequestering agent. For example, in the case of testing for an envelope virus, a "virus positive" result can be used as an indication that the sample should be treated so as to inactivate the envelope virus in the sample. Alternatively, a "virus-positive" result can be used as an indication that the sample should be discarded and no attempt at decontamination should be made. According to such a method, a "virus-negative" result can constitute the result of a first screen of a sample, wherein only after a sample first tests negative is it further contacted with a cholesterol-sequestering agent. Such a two step procedure can provide an additional layer of precaution for "virus-negative" blood so as to reduce the likelihood that a virus may evade a detection method and subsequently infect a transfusion recipient. For example, in some cases an envelope virus may have recently infected a donor so that the virus in a blood sample provided by the donor may not be detectable according to some testing methods.

Aside from whole blood, a blood sample can be processed in a variety of ways to yield blood products that can be administered to an individual. For example, white blood cells can be removed from a blood sample (a process known as "leukoreduction") to thereby remove a population of cells that may be infected with a microorganism such as an envelope virus. In addition to providing a potential vehicle for viral infection, the transfusion of white blood cells can induce reactions in a recipient including, fever, chills and immune reactions that limit the effectiveness of subsequent transfusions. Leukoreduction generally removes greater than 99.9% of the white blood cells from cellular blood components (red cells and platelets). White blood cells can be removed from a blood sample by methods such as filtration (e.g., nano-filtration), affinity adhesion, or specialized centrifugation.

In addition to leukoreduction, a variety of other procedures can be carried out on a blood sample to yield useful blood products. For example, a blood sample can be treated to isolate plasma (fresh frozen plasma), cryoprecipitate, serum, red blood cells (e.g., white blood cell-depleted red blood cells), platelets (e.g., platelet concentrates), granulocytes, or protein components of the blood (e.g., fibrinogen, albumin, a clotting factor, or immunoglobulin). Clotting factors include Factors I, II, V, VII, VIII, IX, X, XI, XII, and XIII, and Von Willebrand Factor.

Blood or a blood product is treated with a cholesterol-sequestering agent and subsequently administered to an individual. The step of contacting the blood or blood product with the cholesterol-sequestering agent can occur at any point during or after the isolation of a blood sample from a donor. For example, a blood sample can be directly collected into an isolation vessel (e.g., a plastic collection bag) that contains an amount of a cholesterol-sequestering agent effective to reduce the load of a microorganism, e.g., an envelope virus, in the blood sample. Alternatively, a cholesterol-sequestering agent can be added to a blood sample following its collection (e.g., after a test is performed to determine the presence or absence of an envelope virus), during the processing of the blood sample, or when the processing has been completed. For example, a leukodepleted blood sample can be contacted with a cholesterol-sequestering agent before and/or after the leukodepletion step. In methods that involve the enrichment or purification of a blood product (e.g., a cell or a protein), the cholesterol-sequestering agent can optionally be added after the enrichment or purification step. Purification of a blood product can be either partial purification or purification to homogeneity. The cholesterol-sequestering agent can remain with the blood or blood product when it is introduced to a recipient.

The amount of a cholesterol-sequestering agent to be used in the methods described herein can vary according to the specific cholesterol-sequestering agent and the amount of microorganism that is to be inactivated. Routine methods can be carried out to determine the optimal dosage of a cholesterol-sequestering agent to be applied to a given sample and a given microorganism. For example, an assay that measures virus infectivity can be used to determine the effect of a given dose of a cholesterol-sequestering agent on that virus. Those doses that reduce or eliminate infectivity of the microorganism (e.g., as measured by infection of the virus in an experimental host cell or animal model) can be used to treat blood or blood products according to the methods described herein.

Reduction or Prevention of Maternal to Fetal Transmission of an Envelope Virus

A cholesterol-sequestering agent can be used to reduce or prevent maternal to fetal transmission of a microorganism, such as an envelope virus, that can occur during birth. In general, a composition containing a cholesterol-sequestering agent is administered to a pregnant individual in an amount effective to reduce or prevent maternal to fetal transmission of the microorganism. The cholesterol-sequestering agent can prevent or reduce transmission of the microorganism resulting from either a vaginal birth or a cesarean section birth. The methods described herein can optionally include a step of diagnosing the pregnant individual as having an infection with the microorganism.

In those embodiments where a cholesterol-sequestering agent is used to prevent or reduce transmission of a microorganism resulting from a vaginal birth, the cholesterol-sequestering agent is administered to the birth canal in an amount effective to reduce or prevent maternal to fetal transmission of the microorganism. In general, the cholesterol-sequestering agent is administered prior to birth and remains present in the birth canal during birth. The cholesterol-sequestering agent can be administered to any or all of the uterus cervix, vagina, and/or vulva in advance of the birth. Repeated administrations of the cholesterol-sequestering agent can optionally be applied as part of a regimen to reduce the load of the microorganism in the birth canal and maintain the microorganism load at low or non-detectable levels at the time of birth. Maternal to fetal transmission of a microorganism such as an envelope virus can result from, for example, the presence of free viral particles and/or virally infected cells in cervical or vaginal secretions and/or in fluids released following the rupture of fetal membranes.

The cholesterol-sequestering agent can optionally be administered in combination with or formulated as a component of a lubricant. A lubricant can assist in child birth by, for example, reducing the frictional forces involved in dilation that can cause damage to maternal tissue and promote maternal to fetal transmission of a microorganism.

In those embodiments where a cholesterol-sequestering agent is used to prevent or reduce transmission of a microorganism resulting from a cesarean section birth, the cholesterol-sequestering agent is administered to the site of a surgical incision in an amount effective to reduce or prevent maternal to fetal transmission of the microorganism. In general, the cholesterol-sequestering agent is administered immediately after the incision for the cesarean section is made. For example, the cholesterol-sequestering agent can be applied directly to the areas of contact between maternal tissues and fetal tissues.

In either a vaginal birth or a cesarean section birth, a cholesterol-sequestering agent can be applied directly to the newborn immediately after birth. For example, the cholesterol-sequestering agent can be applied to an exposed tissue of the newborn such as the umbilical cord.

The application of a cholesterol-sequestering agent directly to the newborn can contribute to the reduction or elimination of a microorganism, e.g., viral particles, that may remain in maternal-derived biological material.

Compositions Containing Cholesterol-Sequestering Agents

As detailed herein, by removing cholesterol from the membrane of a microorganism such as an envelope virus, a cholesterol-sequestering agent not only disrupts the ordered structure of the membrane elements, but further destroys the integrity of the membrane itself leading to disruption of viral membranes and leakage of viral contents into the medium, an irreversible process that can fully inactivate the viral particle. In addition, a cholesterol-sequestering agent can block the fusion of a virus with the plasma membrane and/or block the budding of the virus from lipid rafts on the membrane of the infected cell. Accordingly, a cholesterol-sequestering agent can be used to reduce or prevent maternal to fetal transmission of a microorganism and/or to reduce or eliminate a microorganism present in a blood sample or a blood product.

Envelope viruses that can be targeted using the methods and compositions described herein include, but are not limited to: a human immunodeficiency virus (HIV) such as HIV-1 or HIV-2; a human herpes virus (HHV) such as HHV1, HHV2, HHV3, HHV4, HHV5, HHV6, HHV7, or HHV8; a hepatitis virus such as hepatitis B virus, hepatitis C virus, or hepatitis D virus; a pox virus such as a small pox virus or molluscum contagiosum virus; an orthomyxovirus such as an influenza virus types A, B, or C; a paramyxovirus such as a mumps virus or a parainfluenza virus type 1, 2, 3, or 4; a human T-cell lymphotropic virus (HTLV) such as HTLV type I or II; a togaviruses such as rubella virus, yellow fever virus, or sinbis virus; ebola virus; or a coronavirus such as severe acute respiratory syndrome (SARS) virus.

In addition to envelope viruses, the methods and compositions described herein can be used to reduce or prevent maternal to fetal transmission of a variety of microorganisms, for example, a bacterium (e.g., anthrax or chlamydia), a mycobacterium (e.g., mycobacterium tuberculosis), a virus (an envelope or non-envelope virus, e.g., a protein coated virus such as picorna virus), a fungus, or a protozoan.

The methods and compositions described herein can be used to prevent clinical conditions that result from an infection by en envelope virus, including but not limited to AIDS (HIV infection), certain cancers (caused by HTLV types I and II), fever blisters or cold sores (*Herpes labialis*; HHV1 infection), genital herpes (*Herpes genitalis*; HHV2 infection), chicken pox (HHV3 infection), herpes zoster or shingles (HHV3 infection), mononucleosis (HHV4 infection), cytomegalovirus infection (HHV infection), Kaposi's Sarcoma (HHV8 infection), German measles (rubella virus infection), or severe acute respiratory syndrome (SARS virus infection). These clinical conditions can result from the infection of an individual with an envelope virus as a result of maternal to fetal transmission of the virus or from the administration of blood or a blood product that is contaminated with an envelope virus.

A variety of compositions can be formulated to contain an amount of a cholesterol-sequestering agent effective to reduce or prevent transmission of an envelope virus. In the case of compositions used to reduce or prevent maternal to fetal transmission of a virus, the composition can be formulated for administration to the birth canal. The cholesterol-sequestering agent can be contained in, for example, creams, lotions, ointments, gels, lubricants, liquids, sprays, powders, or absorbent materials.

A composition containing a cholesterol-sequestering agent can also include a pharmaceutically acceptable carrier. As used herein the language "pharmaceutically acceptable carrier" includes solvents, dispersion media, coatings, antiviral agents, antibacterial agents, antifungal agents, isotonic and absorption delaying agents, and the like, compatible with pharmaceutical administration. Supplementary active compounds can also be incorporated into the compositions.

Antimicrobial Compounds

The methods described herein to reduce or prevent maternal to fetal transmission of an envelope virus can be used in combination with one or more anti-microbial agents, e.g., antiviral agents or antibacterial agents. For example, a pregnant individual infected by a virus such as HIV can be treated with an anti-viral agent such as a nucleoside reverse transcriptase inhibitor, a non-nucleoside reverse transcriptase inhibitor, a protease inhibitor, a fusion inhibitor, and/or an integrase inhibitor. The antiviral treatments can be carried out over a period of days, weeks, or months in advance of the birth. Such treatments can be used to reduce viral load in the individual at the time of birth. Accordingly, the effectiveness of the cholesterol-sequestering agent treatments can be enhanced in a pregnant individual wherein viral load has already been reduced by a secondary mechanism.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing maternal to fetal transmission of a microorganism, the method comprising:
    selecting a pregnant individual diagnosed as being infected with a microorganism; and administering to the birth canal of the individual a composition comprising a cholesterol-sequestering agent, wherein the agent is beta-cyclodextrin administered prior to a vaginal birth of a fetus, and wherein an amount of the agent effective to reduce or prevent maternal to fetal transmission of the microorganism remains present in the birth canal during the vaginal birth.

2. The method of claim 1, wherein the beta-cyclodextrin is 2-OH-propyl-beta-cyclodextrin.

3. The method of claim 1, wherein the microorganism is a virus.

4. The method of claim 3, wherein the virus is an envelope virus.

5. The method of claim 4, wherein the envelope virus is a human immunodeficiency virus (HIV).

6. The method of claim 4, wherein the envelope virus is a human herpes virus.

7. The method of claim 4, wherein the envelope virus is a hepatitis virus.

8. The method of claim 4, wherein the envelope virus is a pox virus.

9. The method of claim 4, wherein the envelope virus is an influenza or a parainfluenza virus.

10. The method of claim 4, wherein the envelope virus is a human T-cell lymphotropic virus (HTLV).

11. The method of claim 1, wherein the microorganism enters a cell of a host by endocytosis during at least a portion of its life cycle.

12. The method of claim 11, wherein the microorganism is a bacterium.

13. The method of claim 11, wherein the microorganism is a mycobacterium.

14. The method of claim 11, wherein the microorganism is a fungus.

15. The method of claim 11, wherein the microorganism is a protozoan.

16. The method of claim 1, wherein the composition is formulated as a cream, gel, or lubricant.

17. The method of claim 1, wherein the composition is administered to the birth canal at least one hour before birth.

18. The method of claim 1, wherein the composition is administered to the birth canal at least six hours before birth.

19. The method of claim 1, wherein the composition is administered to the birth canal at least 12 hours before birth.

20. The method of claim 1, wherein the composition is administered to the birth canal less than 72 hours before birth.

21. The method of claim 1, wherein the composition is administered to the birth canal less than 48 hours before birth.

22. The method of claim 1, wherein the composition is administered to the birth canal less than 24 hours before birth.

23. The method of claim 1, wherein a plurality of administrations of the composition are applied to the birth canal within a period of one week prior to the birth.

24. The method of claim 1, wherein a plurality of administrations of the composition are applied to the birth canal within a period of 24 hours prior to the birth.

25. The method of claim 4, further comprising administering to the individual an amount of antiviral agent effective to reduce viral load in the peripheral blood of the individual.

26. The method of claim 25, wherein the antiviral agent is a nucleoside reverse transcriptase inhibitor, a non-nucleoside reverse transcriptase inhibitor, or a protease inhibitor.

27. The method of claim 4, further comprising intravenously administering to the individual prior to the birth an amount of cholesterol-sequestering agent effective to reduce viral load in the individual.

28. The method of claim 1, wherein after cutting of the umbilical cord a newborn is contacted with an amount of the cholesterol-sequestering agent effective to reduce or prevent transmission of the microorganism to the newborn.

29. A method of reducing maternal to fetal transmission of a microorganism, the method comprising:
    selecting a pregnant individual diagnosed as being infected with a microorganism; and administering to the individual a composition comprising a cholesterol-sequestering agent, wherein the agent is beta-cyclodextrin administered to the individual at a site of a surgical incision for a cesarean section birth of a fetus, and wherein an amount of the agent that is effective to reduce or prevent maternal to fetal transmission of the microorganism remains present at the site during the cesarean section birth.

* * * * *